(12) United States Patent
Sugiura et al.

(10) Patent No.: US 8,067,204 B2
(45) Date of Patent: Nov. 29, 2011

(54) LONG-CHAIN CHONDROITIN SUGAR CHAIN AND METHOD FOR PRODUCING THE SAME AND METHOD FOR PROMOTING SYNTHESIS OF CHONDROITIN

(75) Inventors: Nobuo Sugiura, Aichi (JP); Satoshi Shimokata, Higashiyamato (JP); Koji Kimata, Aichi (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 549 days.

(21) Appl. No.: 12/097,725

(22) PCT Filed: Dec. 14, 2006

(86) PCT No.: PCT/JP2006/324961
§ 371 (c)(1),
(2), (4) Date: Jun. 16, 2008

(87) PCT Pub. No.: WO2007/069693
PCT Pub. Date: Jun. 21, 2007

(65) Prior Publication Data
US 2009/0263867 A1    Oct. 22, 2009

(30) Foreign Application Priority Data
Dec. 15, 2005    (JP) .................................. 2005-362526

(51) Int. Cl.
*C12P 19/00*    (2006.01)
(52) U.S. Cl. ........ 435/72; 435/170; 435/193; 435/252.1
(58) Field of Classification Search .................... 435/72, 435/170, 193, 252.1
See application file for complete search history.

(56) References Cited

U.S. PATENT DOCUMENTS

| 2003/0086899 A1* | 5/2003 | Jafari | 424/78.31 |
| 2003/0109693 A1 | 6/2003 | Ninomiya et al. | |
| 2004/0167243 A1* | 8/2004 | Shibata | 522/88 |
| 2009/0068276 A1* | 3/2009 | Main et al. | 424/490 |
| 2010/0196966 A1* | 8/2010 | Frohberg et al. | 435/101 |

FOREIGN PATENT DOCUMENTS

| EP | 1 136 477 | | 9/2001 |
| EP | 1514939 A1 | * | 3/2005 |
| JP | 03 236788 | | 10/1991 |
| JP | 2003-199583 | | 7/2003 |
| WO | WO 03/070960 | | 8/2003 |

OTHER PUBLICATIONS

Zanfardino et al. Microbial Cell Factories (2010) 9:34, 8 pages; from http://www.microbialcellfactores.com/contents/9/1/34.*
Doig et al. Enzyme and microbial Technol. (2003) 32: 347-355.*
Borle et al. Biochim. Biophys. Acta, Biomembranes (1983) 735(1): 131-6; abstract only.*
Definition of surfactant from http://www.freedictionary.com/surfactatn downloaded Dec. 19, 2010.*
Ninomiya, et al. "Molecular Cloning and Characterization of Chondroitin Polymerase from *Escherichia coli* Strain K4," *The Journal of Biological Chemistry*, vol. 277, No. 24, pp. 21567-21575, 2002.
International Search Report dated Dec. 27, 2006.

* cited by examiner

*Primary Examiner* — Susan Hanley
(74) *Attorney, Agent, or Firm* — Knobbe, Martens, Olson & Bear, LLP

(57) ABSTRACT

A method for producing a chondroitin sugar chain comprises reacting a glucuronic acid donor, an N-acetyl galactosamine donor, a sugar receptor and a bacterial cell enzyme which synthesizes chondroitin in the presence of a surfactant. The surfactant is selected from polyoxyethylene octadecyl amine, n-decanoyl-N-methylglucamide, sodium cholate, n-octyl-β-D-thioglucopyranoside, n-nonyl-β-D-thiomaltopyranoside, sucrose monocholate, sucrose monocaprate, and sucrose monolaurate. The chondroitin sugar chain has all the following properties: a weight average molecular weight: 50,000 or more when measured by gel filtration chromatography; it is completely degraded to disaccharides with chondroitinase ABC; and when the sugar chain is decomposed with chondroitinase ABC and the decomposed products are subjected to a disaccharide analysis, substantially all of them correspond to an unsaturated disaccharide unit of chondroitin.

19 Claims, 7 Drawing Sheets ated States Patent

LONG-CHAIN CHONDROITIN SUGAR CHAIN AND METHOD FOR PRODUCING THE SAME AND METHOD FOR PROMOTING SYNTHESIS OF CHONDROITIN

CROSS-REFERENCE TO RELATED APPLICATIONS

This application is the U.S. National Phase under 35 U.S.C. §371 of International Application PCT/JP2006/324961, filed Dec. 14, 2006, which was published in a non-English language, which claims priority to JP 2005-362526, filed Dec. 15, 2005.

BACKGROUND OF THE INVENTION

1. Field of the Invention

The present invention relates to a long-chain chondroitin sugar chain, a method for producing the long-chain chondroitin sugar chain, and a method of promoting chondroitin synthesis.

2. Description of the Related Art

First, abbreviations used in the present application are described.

| | |
|---|---|
| CH: | chondroitin |
| CS: | chondroitin sulfate |
| HA: | hyaluronic acid |
| Glc: | glucose |
| GluUA: | glucuronic acid |
| GlcNAc: | N-acetyl glucosamine |
| GalNAc: | N-acetyl galactosamine |
| GPC: | gel permeation chromatography |
| HPLC: | high performance liquid chromatography |
| K4CP: | chondroitin polymerase derived from *Escherichia coli* K4 strain |
| MALDI-TOF-MS: | Matrix Assisted Laser Desorption/Ionization time-of-flight mass spectrometry |
| UDP: | uridine 5'-diphosphate |

CH is a kind of glycosaminoglycan in which GlcUA and GalNac are linearly and alternately bound by a β1-3 linkage and a β1-4 linkage, respectively. CH is present as CS proteoglycan in a cartilage and many connective tissues in an animal body, and plays important roles in cell adherence, cell generation, cell differentiation, nerve cell extension, cartilage formation, bone formation, tissue regeneration, and the like.

CS is commercially available as useful substances in the form of pharmaceuticals such as a tissue adherence prevention drug, an arthritis therapeutic drug, a drug for low back pain and arthragia, a neuralgia improvement drug, an omarthritis therapeutic drug, an eye dropper, a chronic nephritis therapeutic drug, and an analeptic, a health food, a cosmetic product (a moisturizer), and the like. In general, CS naturally exists as a sugar chain having a weight average molecular weight of 20,000 to 50,000, and it is known that CS's having a weight average molecular weight of 100,000 or more also exist. It is also known that those CS's have a structural characteristic such as a moisture rich characteristic and an ion retention characteristic, and have specific physiological function such as cell adherence and signaling of development and differentiation as an extracellular matrix component owing to their long-chain structure.

A plurality of CH synthetases derived from animals have been cloned. However, those expressed enzymes alone do not have a CH polymerase activity, or have a weak enzymatic activity, even if the enzymes have the CH polymerase activity, so the use of the enzymes does not sufficiently contribute to the efficient industrial production of CH sugar chains. On the other hand, K4CP has also been cloned, and it is known that the enzyme alone has a CH polymerase activity to produce CH efficiently (Patent Document 1 and Non-patent Document 1). However, CH synthesis reaction for a long period by using a recombinant purified enzyme of K4CP results in the production of CH sugar chains having only about 20,000 sugar chains.

Moreover, CH can also be produced by desulfation of CS. However, even if a sugar chain length of a starting material CS is long, sugar chains are cut by a side reaction. The present situation is that commercially available CH's have a weight average molecular weight of 10,000 or less.

A technology of synthesizing a long-chain CH sugar chain has not been known so far. However, from the view point of industrial usability, development of the long-chain CH sugar chain and a production method thereof are expected.

Patent Document 1: JP 2003-199583 A

Non-patent Document 1: Ninomiya, T. et al., 2002, Journal of Biological Chemistry, Volume 277, No. 24, p. 21567-21575

SUMMARY OF THE INVENTION

Problem to be Solved by the Invention

An object of the present invention is to provide a long-chain polymer CH sugar chain and a method for producing the long-chain polymer CH sugar chain.

Means for Solving the Problem

The inventors of the present invention intensively studied to solve the above-mentioned problem. As a result, the inventors found that, in a method of synthesizing a CH from a GlcUA donor, a GalNAc donor, and a sugar receptor by using a CH synthetic enzyme, a CH polysaccharide having much longer sugar chain than that produced by a purified free enzyme can be produced by performing a synthesis reaction using a bacterial strain of *E. coli*, in which a CH synthetic enzyme has been forcibly expressed, as a CH synthetic enzyme in the presence of a surfactant, thus the present invention has been completed.

The present invention provides a production method for a CH sugar chain (hereinafter referred to as "Method 1 of the present invention") comprising at least a step of allowing a GlcUA donor, a GalNAc donor, a sugar receptor, and a bacterial cell enzyme which synthesizes chondroitin to co-exist in a reaction system in the presence of a surfactant.

In Method 1 of the present invention, the bacterial cell enzyme which synthesizes chondroitin is preferably a bacterial cell obtained by expressing a CH polymerase derived from *E. coli*, and the CH polymerase derived from *E. coli* is preferably K4CP.

In Method 1 of the present invention, a host used for the bacterial cell enzyme is preferably *E. coli*, and, particularly, the host is more preferably *E. coli* TOP10 strain.

Further, in Method 1 of the present invention, a surfactant used is preferably selected from the group consisting of Nymeen, MEGA-10, sodium cholate, n-octyl-β-D-thioglucopyranoside, n-nonyl-β-D-thiomaltopyranoside, sucrose monocholate, sucrose monocaprate, and sucrose monolaurate, more preferably selected from the group consisting of Nymeen, n-nonyl-β-D-thiomaltopyranoside, sucrose monocaprate, and sucrose monolaurate, and further more preferably selected from the group consisting of n-nonyl-β-D-thiomaltopyranoside, sucrose monocaprate, and sucrose monolaurate.

In Method 1 of the present invention, the coexistence is preferably performed for 1 hour to 10 days under a condition of 10 to 50° C., more preferably performed for 10 to 30 hours under a condition of 20 to 40° C., still more preferably performed for 15 to 24 hours under a condition of 20 to 40° C., and particularly preferably performed for 15 to 24 hours under a condition of 25 to 37° C.

In Method 1 of the present invention, it is preferred that the GlcUA donor is UDP-GlcUA, and the GalNAc donor is UDP-GalNAc.

In this case, while UDP-Glc4-epimerase and UDP-GlcNAc, and UDP-Glc dehydrogenase and UDP-Glc are allowed to co-exist in a reaction system, the UDP-GalNAc as the GalNAc donor and the UDP-GlcUA as the GlcUA donor can be provided.

In Method 1 of the present invention, one or two or more organic solvents selected from the group consisting of xylene, chloroform, paraffin, and formaldehyde are preferably allowed to co-exist. In particular, chloroform, or chloroform and xylene is/are preferably allowed to co-exist. Moreover, the organic solvents in a coexistence state preferably has a concentration of more than 0% and less than 5%, more preferably has a concentration of more than 0.5% and less than 3%, and further more preferably has a concentration of 1%.

In Method 1 of the present invention, a CH sugar chain to be produced preferably has all the following characteristics (1) to (3):

(1) a weight average molecular weight of 50,000 or more when it is measured by gel filtration chromatography;

(2) completely degradable into disaccharides with chondroitinase ABC; and (3) when the CH sugar chain is decomposed with chondroitinase ABC and the decomposed products are subjected to a disaccharide analysis, substantially all the products correspond to CH unsaturated disaccharides.

A molecular weight of the CH sugar chain produced by Method 1 of the present invention is a weight average molecular weight of preferably 75,000 or more and more preferably 200,000 or more. As ranges of a preferred molecular weight, ranges of 50,000 to 200,000, 50,000 to 500,000, 50,000 to 1,000,000, 75,000 to 200,000, 75,000 to 500,000, 75,000 to 1,000,000, 200,000 to 500,000, 200,000 to 1,000,000, 500,000 to 1,000,000, 500,000 to 1,000,000, and the like can be specifically exemplified.

The present invention also provides a method of promoting CH synthesis (hereinafter referred to as Method 2 of the present invention) comprising allowing a surfactant to co-exist when an enzymatic reaction is performed by a bacterial cell enzyme which synthesizes CH.

The present invention also provides a CH sugar chain (hereinafter referred to as "Sugar chain of the present invention") having all the following characteristics (1) to (3):

(1) a weight average molecular weight of 50,000 or more when it is measured by gel filtration chromatography;

(2) completely degradable into disaccharides with chondroitinase ABC; and (3) when the CH sugar chain is decomposed with chondroitinase ABC and the decomposed products are subjected to a disaccharide analysis, substantially all the products correspond to CH unsaturated disaccharides.

A molecular weight of the sugar chain of the present invention is a weight average molecular weight of preferably 75,000 or more and of more preferably 200,000 or more. As ranges of a preferred molecular weight, ranges of 50,000 to 200,000, 50,000 to 500,000, 50,000 to 1,000,000, 75,000 to 200,000, 75,000 to 500,000, 75,000 to 1,000,000, 200,000 to 500,000, 200,000 to 1,000,000, 500,000 to 1,000,000 and the like can be specifically exemplified.

Effects of the Invention

Method 1 of the present invention is very useful because the method enables the production of a polymer CH sugar chain which has a weight average molecular weight similar to or more than that of a naturally-existing polymer CS that is known to have a specific physiological activity. Method 2 of the present invention is very useful because a CH sugar chain can be very efficiently produced. Furthermore, a sugar chain of the present invention is a polymer CH that cannot be usually found among CH's extracted from an animal tissue. The sugar chain of the present invention is very useful, because the sugar chain is expected to have specific physical property and a physiological activity, and can be a material for a pharmaceutical, a health food, a cosmetic product, and the like.

DETAILED DESCRIPTION OF THE INVENTION

Figure 1:
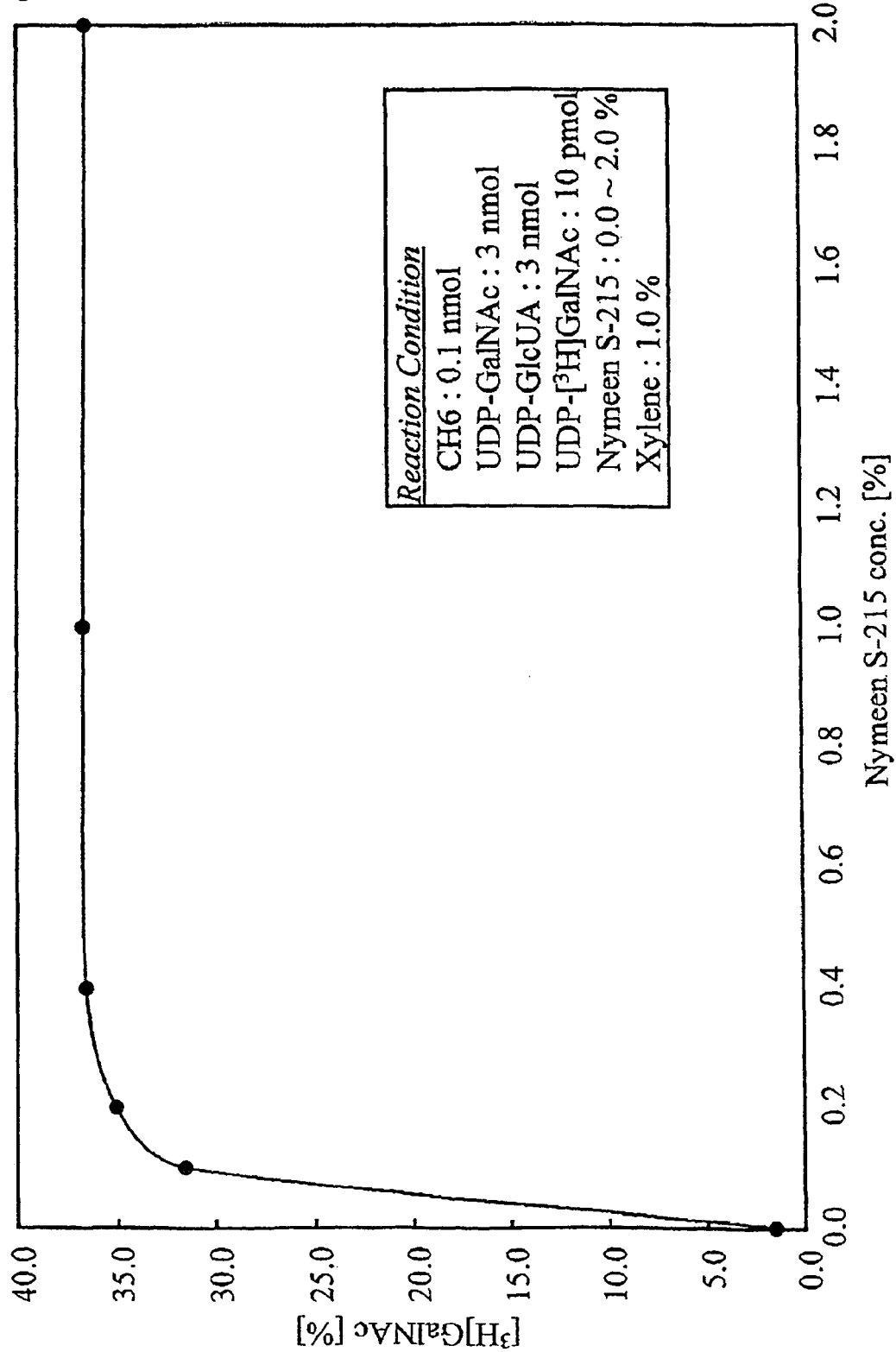
FIG. 1 shows the dependence of CH synthesis on surfactant concentration.

The present invention is described in detail hereinbelow by way of the best mode for carrying out the invention in an order of Method 1 of the present invention, Method 2 of the present invention, and Sugar chain of the present invention.

<1> Method 1 of the Present Invention

Method 1 of the present invention is a method for producing a CH sugar chain comprising at least a step of allowing a GlcUA donor, a GalNAc donor, a sugar receptor, and a bacterial cell enzyme which synthesizes CH to co-exist in a reaction system in the presence of a surfactant, that is, comprising at least a step in which a GlcUA residue of a GlcUA donor and a GalNAc residue of a GlaNAc donor are alternately transferred to a sugar receptor by using a bacterial cell enzyme which synthesizes CH as a reaction enzyme to thereby produce a CH sugar chain.

The "GlcUA donor" used herein is not limited as long as the donor is a molecule capable of donating a GlcUA residue to a sugar chain molecule, and a GlcUA nucleotide is preferred. As the GlcUA nucleotide, UDP-GlcUA, and dTDP (deoxythymidine-5'-diphosphate)-GlcUA can be exemplified, and the UDP-GlcUA is preferred.

Further, the "GalNAc donor" used herein is not limited as long as the donor is a molecule capable of donating a GalNAc residue to a sugar chain molecule, and a GalNAc nucleotide is preferred. As the GalNAc nucleotide, UDP-GalNAc, dTDP (deoxythymidine5'-diphosphate)-GalNAc can be exemplified, and the UDP-GalNAc is preferred.

These sugar nucleotides can be produced by a known method, or commercially available.

Further, as the sugar receptor used in Method 1 of the present invention, there are exemplified sugar chains each represented by the following general formulae (1) and (2).

GlcUA-R$^1$  (1)

GalNAc-R$^2$  (2)

where - represents a glycoside linkage and R$^1$ and R$^2$ each represent an arbitrary group, which may be the same or different from each other.

As "R$^1$" and "R$^2$", a sugar chain residue having a CH backbone and a sugar chain residue having an HA backbone can be exemplified. Examples of the sugar chain residue having a CH backbone described herein include a CH residue and a CS residue. These sugar chain residues may be further bound to another chemical substance or the like.

Moreover, a sugar chain size of the sugar receptor is not particularly limited, and oligosaccharides having about 1 to 50 saccharides, preferably oligosaccharides having about 1 to 40 saccharides, more preferably oligosaccharides having about 1 to 30 saccharides, and still more preferably oligosaccharides having about 1 to 20 saccharides can be exemplified. More specifically, CH disaccharide, CH trisaccharide, CH tetrasaccharide, CH pentasaccharide, CH hexasaccharide, CH heptasaccharide, CH octosaccharide, CH nonasaccharide, CH decasaccharide, and the like can be exemplified. As "R$^1$" in the general formula (1) and "R$^2$" in the general formula (2), CH oligosaccharides and HA oligosaccharides each having the above-mentioned size can be used.

In addition, GlcUA as a non-reducing end saccharide residue in the general formula (1) preferably has a β structure. When the GlcUA residue is bound to GlcNAc or GalNAc in the R$^1$ group, the glycoside linkage thereof preferably has a β1-3 structure. GalNAc as a non-reducing end saccharide residue in the general formula (2) also preferably has a β structure. When the GalNAc residue is bound to GlcUA in the R$^2$ group, the glycoside linkage thereof preferably has a β1-4 structure.

These sugar receptors can be produced by a known method or commercially available.

A bacterial cell enzyme that synthesizes CH used in Method 1 of the present invention is not particularly limited as long as it is a bacterial cell enzyme having an activity of synthesizing CH.

The bacterial cell enzyme in the present application means a bacterium itself capable of exhibiting the specific enzymatic activity while a bacterial morphology is retained. That is, a bacterial cell enzyme which synthesizes CH means a bacterium capable of exhibiting the enzymatic activity to synthesize CH while a bacterial morphology is retained.

The bacterial cell enzyme which synthesizes CH is preferably a bacterial cell obtained by introducing the CH polymerase gene derived from E. coli (a bacterial cell obtained by expressing the CH polymerase gene derived from E. coli). A bacterial cell which is prepared by introducing the gene obtained from E. coli having genes involved in production of capsule polysaccharide is preferred. The use of a bacterial cell obtained by expressing K4CP is very preferred. As a host, E. coli is preferably used. In particular, E. coli TOP10 strain is more preferable.

"K4CP" described herein is a polymerase capable of extending a CH by: reacting a CH as a receptor substrate with GalNAc nucleotide (such as UDP-GalNAc) and GlcUA nucleotide (such as UDP-GlcUA) as donor substrates; linking GalNAc to a non-reducing end of the receptor substrate when the non-reducing end is a GlcUA residue, or linking GlcUA to a non-reducing end of the receptor substrate when the non-reducing end is a GalNAc residue; thereby linking the GalNAc and GlcUA alternately (Non-patent Document 1 and Patent Document 1).

In Method 1 of the present invention, a production method of DNA and an origin of DNA to be introduced into E. coli to expresses a CH polymerase activity are not particularly limited. For example, K4CP was originally obtained from E. coli having a K4 antigen, but K4CP may be obtained from other transformed biological species, or a DNA produced by chemical synthesis or the like may also be used.

Moreover, in the Region 2 (R-II) of K4 antigen-specific synthesis-related gene cluster in an E. coli K4 strain, there are useful genes related to synthesis of a CH other than K4CP. KfoA that is the first ORF was identified as the gene of UDP-Glc-4-epimerase having an activity of converting UDP-GlcNAc to UDP-GalNAc. KfoF that is the seventh ORF was identified as the gene of UDP-Glc dehydrogenase having an activity of converting UDP-Glc to UDP-GlcUA.

Therefore, by using an activity of epimerase encoded by KfoA and an activity of dehydrogenase encoded by KfoF, a CH polymer can be synthesized from UDP-GlcNAc and UDP-Glc as substrates, which are cheaper than UDP-GalNAc and UDP-GlcUA. That is, in Method 1 of the present invention, a CH sugar chain can be produced by: allowing UDP-Glc-4-epimerase and UDP-GlcNAc, and UDP-Glc dehydrogenase and UDP-Glc to co-exist in a reaction system; and providing UDP-GalNAc as a GalNAc donor and UDP-GlcUA as a GlcUA donor (see Examples 7 to 9 described below).

It is known that UDP-GlcNAc and UDP-Glc can be synthesized from a monosaccharide such as Glc or the like by a known enzymatic or bacterial reaction, so it is expected that a CH sugar chain can be industrially produced from a more inexpensive material.

Forms of the above-mentioned UDP-Glc-4-epimerase and UDP-Glc dehydrogenase are not particularly limited. The form is preferably a bacterial cell enzyme as in the case of K4CP. Therefore, by using a bacterial reactor of a recombinant enzyme produced by KfoA E. coli expression system or KfoF E. coli expression system in addition to a K4CP expression system, a long-chain CH can be synthesized from UDP-GlcNAc and UDP-Glc. Thus, because the long-chain CH can be synthesized from an inexpensive material, both time and cost required for purification of an enzyme can be eliminated, which leads to provision of amass synthesis method for a long-chain CH, which is very advantageous for the industrial production.

As a vector for introducing these DNAs, a suitable vector (phage vector, plasmid vector, or the like) that is capable of expressing an introduced DNA can be used, so a vector can be appropriately selected depending on host cells into which the vector of the present invention is introduced. As the above-mentioned host-vector system, the following combination can be exemplified: a combination of mammalian cells such as COS cells and 3LL-HK46 cells and an expression vector for mammalian cells such as pGIR201 (Kitagawa, H., and Paulson, J. C. (1994) J. Biol. Chem. 269, 1394-1401), pEF- BOS (mizushima, S., and Nagata, S. (1990) Nucleic Acid Res. 18, 5322), pCXN2 (Niwa, H., Yamamura, K. and Miyazaki, J. (1991) Gene 108, 193-200), pCMV-2 (manufactured by Eastman Kodak Company), pCEV18, pME18S (Maruyama et al., Med. Immunol., 20, 27 (1990)), or pSVL (manufactured by Pharmacia Biotech Inc.), and a combination of *E. coli* and an expression vector for prokaryotic cells such as pTrcHis (manufactured by Invitrogen Corporation), pGEX, pTrc99, pKK233-3, pEZZZ18, pCH110, (manufactured by Pharmacia Biotech Inc.), pET (manufacture by Stratagene), pBAD, pRSET, and pSE420 (manufactured by Invitrogen Corporation). Other examples of the host cells include insect cells, yeast, and *Bacillus subtilis*, and various vectors corresponding to these host cells can be exemplified. Of the above-mentioned host-vector system, the combination of *E. coli* and pTrcHis is preferred.

In addition, these DNAs and expression vectors include a secretion type, an intracellular production type, and the like, and the intracellular production type in which enzyme molecules is expressed in cells is preferred.

A promoter of the expression vector can be suitably selected, and lac promoter whose expression can be induced by β-isopropylthiogalactoside is preferred. In order to retain the active enzyme structure in cells, trc promote is also preferred, because the trc promoter does not tend to form an inclusion body in a denatured precipitate form, and has relatively low expression efficiency.

The bacterial cell enzyme used in Method 1 of the present invention can be prepared by a known method that is suitably selected by those skilled in the art. Specific methods can be referred to Example 1 described below.

In Method 1 of the present invention, a surfactant used is preferably selected from the group consisting of Nymeen, MEGA-10, sodium cholate, n-octyl-β-D-thioglucopyranoside, n-nonyl-β-D-thiomaltopyranoside, sucrose monocholate, sucrose monocaprate, and sucrose monolaurate. Of those, the surfactant is preferably selected from the group consisting of Nymeen, n-nonyl-β-D-thiomaltopyranoside, sucrose monocaprate, and sucrose monolaurate. It is very preferred that the surfactant is selected from the group consisting of n-nonyl-β-D-thiomaltopyranoside, sucrose monocaprate, and sucrose monolaurate.

"Coexistence" in Method 1 of the present invention is not particularly limited as long as a reaction system is formed, in which the donor molecules, sugar receptor molecule, and the bacterial cell enzyme are contacted with each other to thereby cause an enzyme reaction by the bacterial cell enzyme. For example, the donor molecules, sugar receptor molecule, and bacterial cell enzyme may co-exist in a solution. Alternatively, the coexistence may be also attained by: immobilizing the bacterial cell enzyme on a suitable solid phase (such as beads, an ultrafiltration membrane, and a dialysis membrane); and continuously bringing the solid phase into contact with a solution containing the donors and the receptor. For example, a column-type reactor, a membrane-type reactor, or the like can be adopted. Further, the method shown in WO 00/27437 can be also used, in which a receptor is immobilized to a solid phase to undergo an enzyme reaction. Still further, a bioreactor or the like which regenerates (synthesizes) a donor may be used in combination.

In Method 1 of the present invention, the coexistence is preferably performed for 1 hour to 10 days under a condition of 10 to 50° C., more preferably performed for 10 to 30 hours under a condition of 20 to 40° C., still more preferably performed for 15 to 24 hours under a condition of 20 to 40° C., and particularly preferably performed for 15 to 24 hours under a condition of 25 to 37° C.

The coexistence is preferably performed in the state where temperature and pH are kept constant. In order to keep the pH constant, the reaction is preferably carried out in a buffer solution having a buffer action in the predetermined pH range. In Method 1 of the present invention, the pH range suitable for the coexistence is a pH range of 5 to 9, preferably a pH range of 6 to 8, and more preferably a near-neutral range.

In Method 1 of the present invention, the GlcUA and the GalNAc are preferably D-GlcUA and D-GalNAc, respectively. In the general formula of Method 1 of the present invention, the glycoside linkage between GlcUA and GalNAc (GlcUA-GalNAc) is preferably a β1-3 linkage, and the glycoside linkage between GalNAc and GlcUA (GalNAc-GlcUA) is preferably a β1-4 linkage.

When the coexistence is performed, an organic solvent may also be allowed to co-exist. One or two or more organic solvents selected from the group consisting of xylene, chloroform, paraffin, and formaldehyde are preferably allowed to co-exist. In particular, chloroform or "chloroform and xylene" is preferably allowed to co-exist. Moreover, the concentration of organic solvents in a coexistence state is preferably more than 0% and less than 5%, more preferably more than 0.5% and less than 3%, and further more preferably 1%.

In addition, a CH derivative having high molecular chain length can also be produced by Method 1 of the present invention, in which a sugar chain derivative having a GlcUA β1-3 structure or a GalNAc β1-4 structure at a non-reducing end thereof is used as a sugar receptor. The sugar chain derivative described herein means, for example, a sugar receptor represented by the formulae (1) and (2) which has a sugar chain other than a CH, or has an arbitrary organic group other than a sugar chain, or the like, as $R^1$ and $R^2$. The CH derivative having a polymer chain length means a CH derivative in which a sugar chain other than CH, or an arbitrary organic group other than a sugar chain are bound to a CH having a high molecular chain length.

Further, in Method 1 of the present invention, a CH sugar chain to be produced preferably has all the following characteristics (1) to (3):

(1) a weight average molecular weight of 50,000 or more when it is measured by gel filtration chromatography, and the conditions for gel filtration chromatography can be referred to Examples.

(2) completely degradable into disaccharides with chondroitinase ABC; and (3) when the CH sugar chain is decomposed with chondroitinase ABC and the decomposed products are subjected to a disaccharide analysis, substantially all the products correspond to CH unsaturated disaccharides.

In this case, the sugar receptor used is required to be a sugar chain in which each of "$R^1$" an "$R^2$" has a CH backbone alone in the following general formulae (1) or (2).

$$\text{GlcUA-}R^1 \qquad (1)$$

$$\text{GalNAc-}R^2 \qquad (2)$$

where - represents a glycoside linkage, and $R^1$ and $R^2$ each represent an arbitrary group, which may be the same or different from each other.

The chondroitinase ABC described herein is an enzyme which is one kind of glycosaminoglycan-decomposing enzymes, and reacts to a CH and an HA, to decompose them completely into unsaturated disaccharides having hexosamine at a non-reducing end thereof.

The term "substantially all" used herein means a case where peaks other than CH unsaturated disaccharide cannot be detected by normal HPLC when the above-mentioned decomposed products are subjected to a disaccharide analysis.

A molecular weight of the CH sugar chain produced by Method 1 of the present invention is not particularly limited. Method 1 of the present invention can be used for production of a CH sugar chain having a weight average molecular weight of 50,000 or more, preferably a CH sugar chain having a weight average molecular weight of 75,000 or more, and particularly preferably a CH sugar chain having a weight average molecular weight of 200,000 or more. The upper limit of the molecular weight is not particularly limited. For example, a CH sugar chain having a weight average molecular weight of about 500,000 or about 1,000,000 can also be produced. Therefore, as ranges of a preferred molecular weight, ranges of 50,000 to 200,000, 50,000 to 500,000, 50,000 to 1,000,000, 75,000 to 200,000, 75,000 to 500,000, 75,000 to 1,000,000, 200,000 to 500,000, 200,000 to 1,000,000, 500,000 to 1,000,000, and the like can be specifically exemplified.

<2> Method 2 of the Present Invention

Method 2 of the present invention is a method of promoting CH synthesis comprising allowing a surfactant to co-exist when an enzymatic reaction is performed by a bacterial cell enzyme which synthesizes CH.

Method 2 of the present invention is, for example, based on a finding that, in a production method of a CH sugar chain like Method 1 of the present invention, synthesis of a CH is promoted when an enzyme reaction of a bacterial cell enzyme which synthesizes CH is carried out in the presence of a surfactant. Each meaning of terms "bacterial cell enzyme which synthesizes CH", "surfactant", and "coexistence" is the same as the terms used for describing Method 1 of the present invention.

Besides, when Method 2 of the present invention is carried out in the same manner as Method 1 of the present invention, each description about a GlcUA donor, a GalNAc donor, and a sugar receptor, a description about a CH sugar chain to be synthesized, and descriptions about other various conditions and the like are the same as those in Method 1 of the present invention.

<3> Sugar Chain of the Present Invention

A CH sugar chain of the present invention is a sugar chain having all the following characteristics (1) to (3):

(1) a weight average molecular weight of 50,000 or more when it is measured by gel filtration chromatography, and the conditions for gel filtration chromatography can be referred to Examples.

(2) completely degradable into disaccharides with chondroitinase ABC; and (3) when the CH sugar chain is decomposed with chondroitinase ABC and the decomposed products are subjected to a disaccharide analysis, substantially all the products correspond to CH unsaturated disaccharides.

A molecular weight of the sugar chain of the present invention is not particularly limited. The sugar chain usually has a weight average molecular weight of 50,000 or more, preferably 75,000 or more, and more preferably 200,000 or more. The upper limit of the sugar chain of the present invention is not particularly limited. The sugar chain can have a molecular weight of about 500,000 or about 1,000,000 as a weight average molecular weight. Therefore, as ranges of a molecular weight of the sugar chain of the present invention, ranges of 50,000 to 200,000, 50,000 to 500,000, 50,000 to 1,000,000, 75,000 to 200,000, 75,000 to 500,000, 75,000 to 1,000,000, 200,000 to 500,000, 200,000 to 1,000,000, 500,000 to 1,000,000, and the like can be specifically exemplified.

State of the sugar chain of the present invention is also not particularly limited. The sugar chain may be in the state of a solution, in the state of a solid (such as a powder, a frozen solution, etc.), or the like.

The meaning of the term "chondroitinase ABC" used for the sugar chain of the present invention is the same as described in Method 1 of the present invention.

The sugar chain of the present invention may be produced, for example, by using Method 1 of the present invention.

EXAMPLES

Hereinafter, the present invention is specifically described in detail with reference to examples. However, the scope of the present invention is not restricted to the examples.

Example 1

Preparation of a Bacterial Cell Enzyme

According to the method described in Japanese Patent Application No. 2003-199583, the gene of the CH polymerase (K4CP) enzyme derived from $E.$ $coli$ and an expression vector were prepared. the plasmid pTrcHis (manufactured by Invitrogen Corporation) was used as the expression vector. The expression vector obtained by the method was introduced to $E.$ $coli$. The $E.$ $coli$ was cultured at 37° C. in an ampicillin-containing LB medium until absorbance of the culture medium reached about 0.6 at a wavelength of 600 nm. β-isopropylthiogalactoside (IPTG), which is an expression induction molecule, was added to the culture medium in such an amount that attains a final concentration of 1 mM, and culture was further performed at 37° C. for 3 hours to induce an enzyme expression. 1 ml of the culture medium was taken and transferred to a centrifugation tube to undergo centrifugation at 10,000 rpm for 1 minute. After the supernatant was discarded, a cell precipitate was used a bacterial cell enzyme. Further, the cell precipitate can maintain the enzymatic activity at least for 1 year by storing at −80° C.

Example 2

Preparation of CH Hexasaccharide (CH6)

To a CH obtained by chemical desulfation (manufactured by SEIKAGAKU CORPORATION), hyaluronidase derived from sheep testis (manufactured by Sigma-Aldrich Corporation) was added, and the limited degradation was performed in a sodium acetate buffer solution containing NaCl, whereby CH oligosaccharides composed of the even number saccharides and having a GlcUA residue at a non-reducing end thereof were obtained. The obtained oligosaccharides were purified by gel filtration and ion-exchange column to collect a fraction corresponding to CH6. The obtained fraction was freeze-dried and subjected to the determination of the uronic acid content (carbazole method), HPLC (GPC), MALDI-TOF-MS, and disaccharide analysis after chondroitinase treatment. As a result, it was confirmed that the obtained fraction was a hexasaccharide having a GalNAc residue at a reducing end thereof and a GlcUA residue at a non-reducing end thereof.

Example 3

Evaluation of the Concentration of Surfactants

To the bacterial cell enzyme obtained in Example 1, 50 mM of Tris-HCl (pH of 7.2) buffer solution containing 20 mM of MnCl$_2$, 150 mM of NaCl, 0.1 nmol of CH6, 3 nmol of UDP-GalNAc, 0.2 µCi of UDP-[$^3$H] GalNAc, and 3 nmol of UDP-GlcUA, and a surfactant (Nymeen S-215; manufactured by NOF CORPORATION) at a final concentration of 0, 0.1, 0.2, 0.4, 1.0, or 2.0% was added and suspended. Each of the suspensions was shaken at 30° C. for 15 hours. After the reaction, each of the suspensions was heat-treated for 10 minutes in boiling water, and then centrifuged at 15,000 rpm for 5 minutes to remove a precipitate. Each of the supernatants was subjected to gel filtration using Superdex peptide HR 10/30 column (manufactured by Amersham Biosciences Co., Ltd.). The sugar chains in each of the eluted solutions were detected based on the absorbance at 225 nm.

An eluted fraction which corresponds to the absorption peak residing in a polymer region was obtained, and an incorporation of [$^3$H] GalNAc was detected. The incorporation was shown by the ratio (%) of the incorporated radioactivity with respect to the total radioactivity as 100%. The results are shown in FIG. 1.

As a result, it was indicated that about 37% of [$^3$H] GalNAc was incorporated into the polymer fraction by setting the concentration of the surfactant at 0.4% or more at the time of the enzyme reaction. On the other hand, when the bacterial cell enzyme was used without addition of the surfactant Nymeen S-215, the incorporation of [$^3$H] GalNAc was rarely observed (FIG. 1).

Example 4

Synthesis of a Long-Chain CH Sugar Chain Using the Bacterial Cell Enzyme and Molecular Weight Analysis CH sugar chain was synthesized in the same manner as in Example 3 with a surfactant Nymeen S-215 set at a final concentration of 0.4%. As a result, it was reconfirmed that about 37% of used [$^3$H] GalNAc was incorporated into a polymer fraction. After the polymer fraction was treated in the same manner as in Example 3, the supernatant was subjected to gel filtration using Superdex peptide HR 10/30 column (manufactured by Amersham Biosciences Co., Ltd.). The detection was carried out in the same manner as in Example 3. After that, the fraction was treated with chondroitinase ABC (manufactured by SEIKAGAKU CORPORATION), and as a result, the fraction was completely made into low-molecular weight compounds. The degradation product obtained by the treatment was subjected to a disaccharide analysis. As a result, it was confirmed that all the decomposed products correspond to CH unsaturated disaccharides. Therefore, the polymer fraction was confirmed to be CH. In addition, it was shown that the polymer CH can be very efficiently produced by setting a concentration of the surfactant to 0.4% or more at the time of the enzyme reaction.

Figure 2:
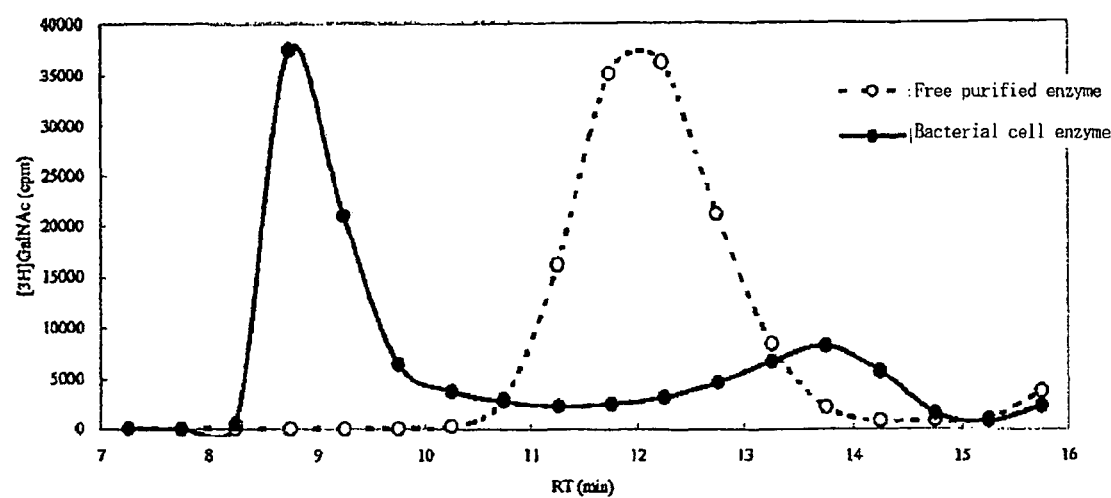
FIG. 2 shows the elution curves of reaction supernatants obtained in Example 4 when the elution was performed with Superdex Peptide column.

The elution pattern of the obtained polymer fractions with Superdex peptide HR10/30 column is shown in FIG. 2. The peak of the obtained polymer fractions was eluted in the void volume fraction with Superdex peptide HR10/30 column (closed circles in FIG. 2). The elimination limit of the column is a weight average molecular weight of 20,000 when the elimination limit is measured using a standard HA, so it was presumed that the obtained polymer fraction (CH polymer) had a weight average molecular weight of 20,000 or more.

On the other hand, after the reaction was performed in the same manner as described above using purified free recombinant K4CP (produced by the method described in Patent Document 1 and Non-patent Document 1), CH having a weight average molecular weight of 5,000 was synthesized (open circles in FIG. 2).

Example 5

Synthesis of a Long-Chain CH Sugar Chain Using the Bacterial Cell Enzyme and Molecular Weight Analysis The following synthesis and molecular weight analysis were carried out to study in more detail a molecular weight of the CH polymer synthesized by the method of the present invention.

Figure 3:
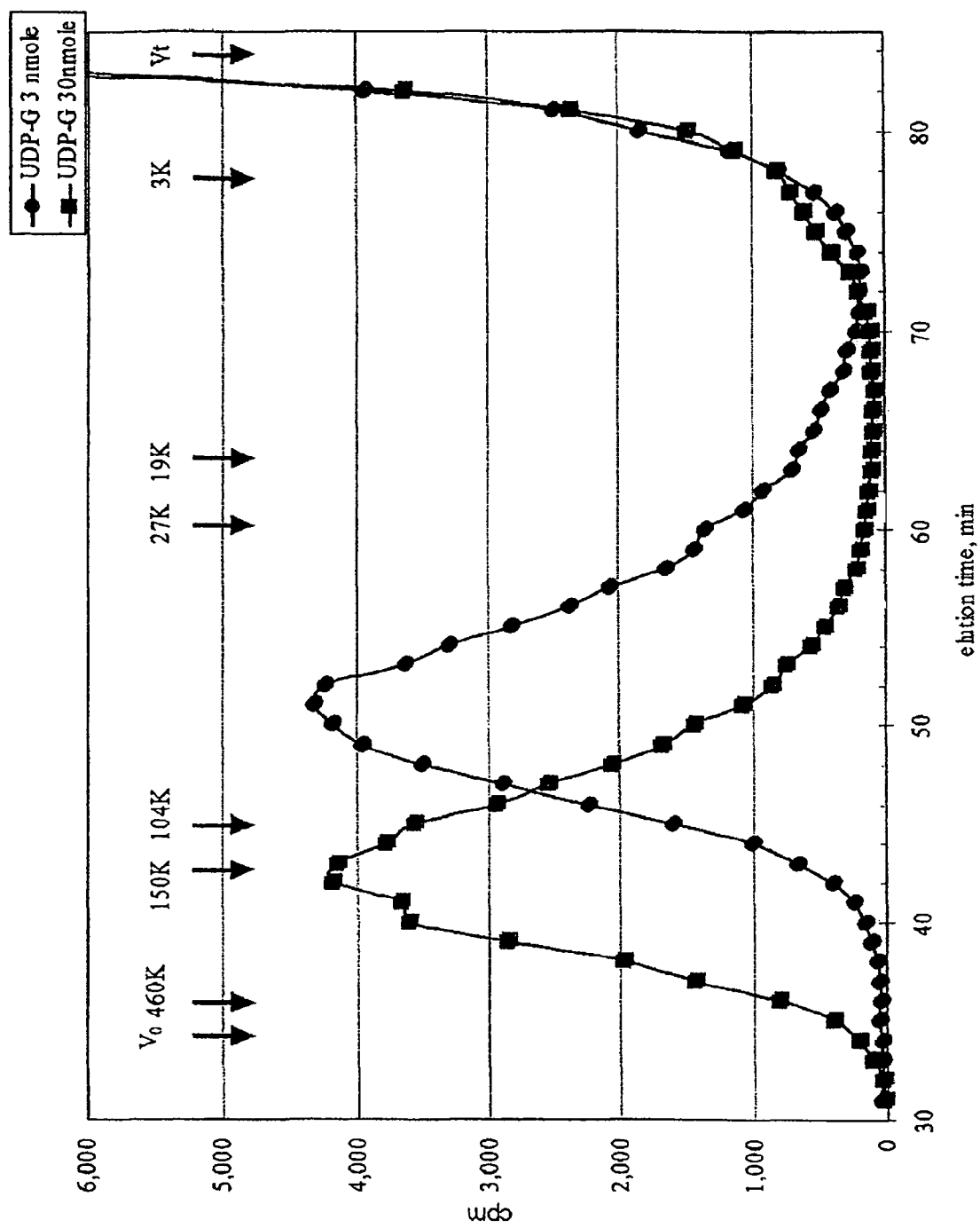
FIG. 3 shows the elution curves of reaction supernatants when the elution was performed with in-line column of Sephacryl S500 and Superose 6.

That is, the CH polymers obtained by using the bacterial cell enzyme in the same manner as in Example 4 and the CH polymers synthesized in the same condition as Example 4 except that concentrations of UDP-GlcUA and UDP-GalNAc were changed to 30 nmol were each loaded to Sephacryl S500 HR 10/30 column and Superose 6 HR 10/30 column linearly connected to each other. As a result, the former was eluted at the position of a weight average molecular weight of 75,000 (closed circles in FIG. 3) with respect to a standard HA as an indicator, and the latter was eluted at the position of a weight average molecular weight of 200,000 (closed squares in FIG. 3).

Example 6

Study of Kinds of Surfactants at the Time of the Enzyme Reaction

The same test as Example 3 was performed using various kinds of surfactants each having a final concentration of 0.4% to examine how various kinds of surfactants influence on the incorporation of [$^3$H] GalNAc. As an enzyme, the bacterial cell enzyme produced in Example 1 was used. Further, the surfactants used are described below.

Nymeen S-215 (polyoxyethylene octadecyl amine, manufactured by NOF Corp.)
Triton X-100 (polyethylene glycol mono-p-isooctyl phenyl ether, manufactured by NAKARAI TESUKU KK)
Tween20 (polyoxyethylene sorbitan monolaurate, manufactured by NAKARAI TESUKU KK)
Tween 80 (polyoxyethylene sorbitan monooleate, manufactured by NAKARAI TESUKU KK)
Brij 35 (polyoxyethylene lauryl ether, manufactured by NAKARAI TESUKU KK)
Brij 58 (polyoxyethylene hexadecyl ether, manufactured by NAKARAI TESUKU KK)
Nonidet P-40 (nonidet P-40, manufactured by NAKARAI TESUKU KK)
Tergitol NP-40 (tergitol NP-40, manufactured by NAKARAI TESUKU KK)
CHAPS (3-[(3-cholamidepropyl)dimethylammonio]-1-propane sulfonate, manufactured by Dojindo)
Octyl-thioglucoside (n-octyl-β-D-thioglucopyranoside, manufactured by KISHIDA CHEMICAL CO., LTD.)
Dodecyl-maltoside (n-dodecyl-β-D-maltopyranoside, manufactured by KISHIDA CHEMICAL CO., LTD.)
MEGA-9 (n-nonanoyl-N-methylglucamide, manufactured by KISHIDA CHEMICAL CO., LTD.)
MEGA-10 (n-decanoyl-N-methylglucamide, manufactured by KISHIDA CHEMICAL CO., LTD.)
CHAPSO (3-[3-cholamidepropyl)dimethylammonio]-2-hydroxy-1-propane sulfonate, manufactured by KISHIDA CHEMICAL CO., LTD.)

Sodium cholate (sodium cholate, manufactured by KISHIDA CHEMICAL CO., LTD.)
LDS (lithium dodecyl sulfate, manufactured by KISHIDA CHEMICAL CO., LTD.)
SDS (sodiumdodecyl sulfate, manufactured by KISHIDA CHEMICAL CO., LTD.)
Octyl-glucoside (n-octyl-3-D-glucopyranoside, manufactured by KISHIDA CHEMICAL CO., LTD.)
Heptyl-thioglucoside (n-heptyl-β-D-thioglucopyranoside, manufactured by KISHIDA CHEMICAL CO., LTD.)
Nonyl-thiomaltoside (n-nonyl-β-D-thiomaltopyranoside, manufactured by KISHIDA CHEMICAL CO., LTD.)
Sucrose monocholate (Sucrose monocholate, manufactured by KISHIDA CHEMICAL CO., LTD.)
Sucrose monocaprate (Sucrose monocaprate, manufactured by KISHIDA CHEMICAL CO., LTD.)
Sucrose monolaurate (Sucrose monolaurate, manufactured by KISHIDA CHEMICAL CO., LTD.)

Figure 4:
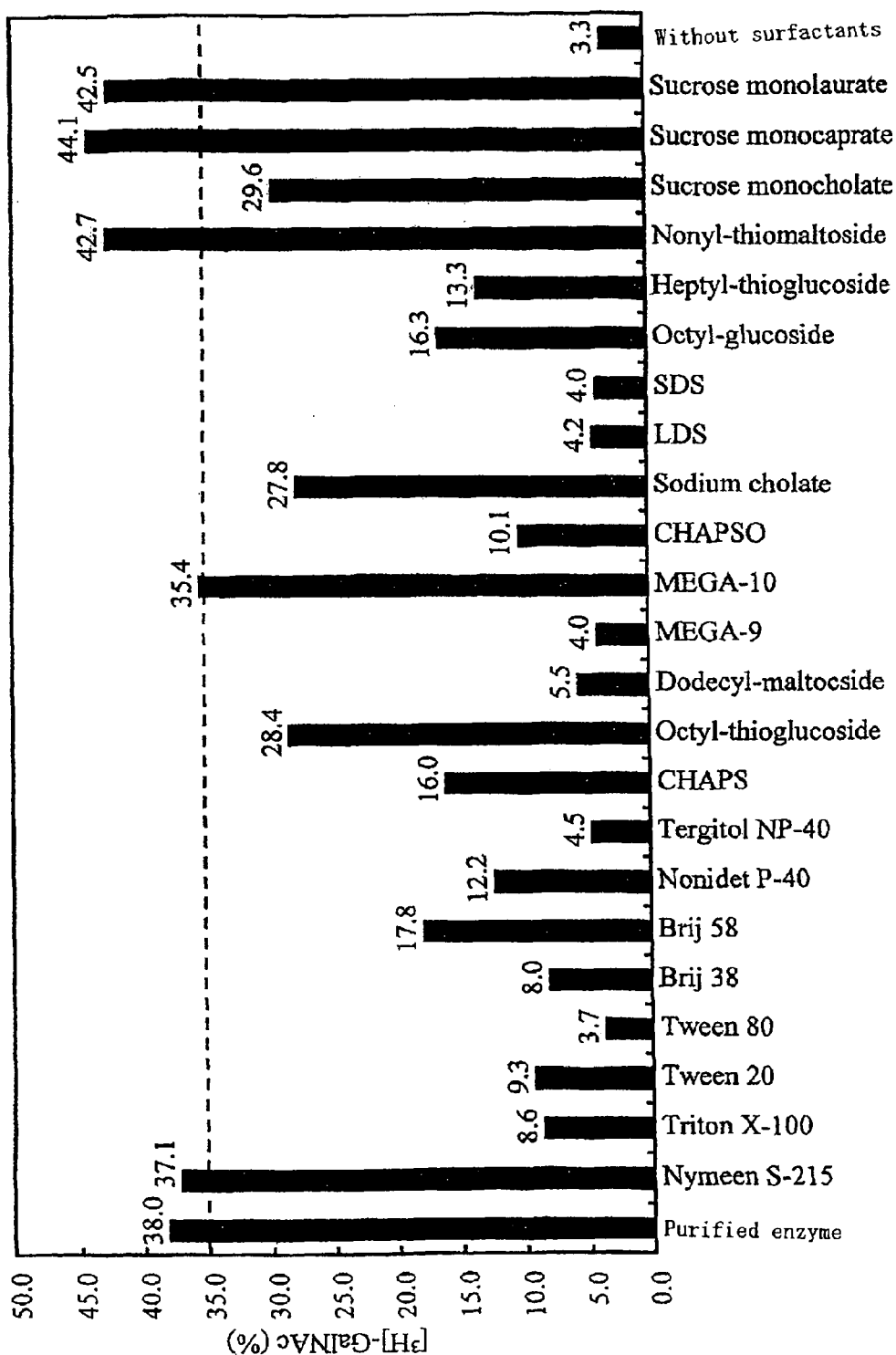
FIG. 4 shows the influence of various surfactants having a final concentration of 0.4% on CH synthesis.

As shown in FIG. 4, it was shown that the use of sucrose monocaprate, n-nonyl-β-D-thiomaltopyranoside, or sucrose monolaurate contributed to particularly efficient incorporation of [$^3$H] GalNAc when the bacterial cell enzyme was used.

Example 7

Figure 5:
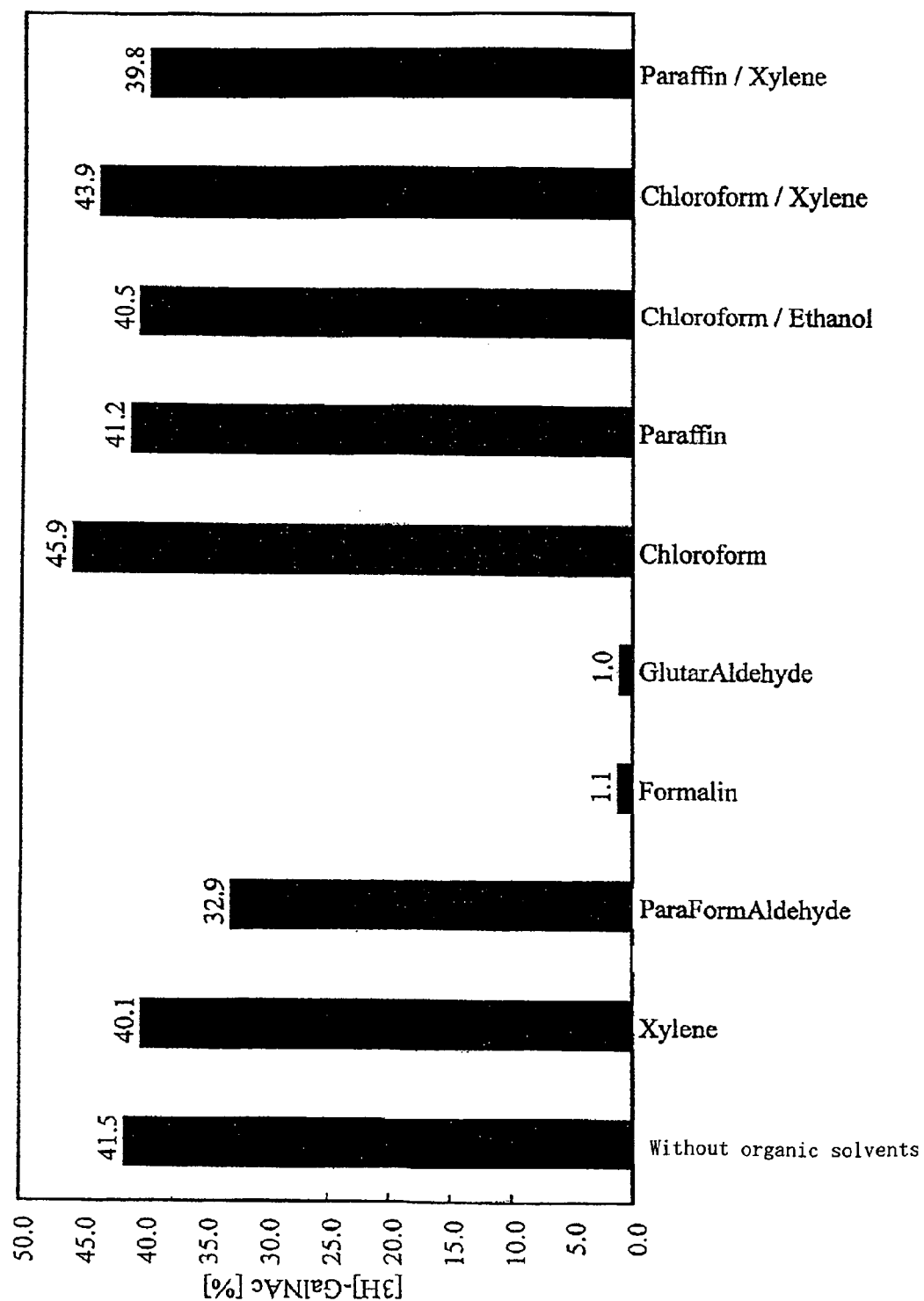
FIG. 5 shows the influence of organic solvents on CH synthesis.

Evaluation of the Influence of Organic Solvents at the Time of the Enzyme Reaction The same test as Example 3 was performed using various kinds of organic solvents each having a final concentration of 1% to examine the influence of the various kinds of organic solvents on the incorporation of [$^3$H] GalNAc. As an enzyme, the bacterial cell enzyme prepared in Example 1 was used. Further, the organic solvents used are described below.
Xylene
Paraformaldehyde
Formalin
Glutaraldehyde
Chloroform
Paraffin
Chloroform/ethanol mixed liquid
Chloroform/xylene mixed liquid
Paraffin/xylene mixed liquid The incorporation was shown by the ratio (%) of the incorporated radioactivity with respect to the total radioactivity of [$^3$H] GalNAc used as 100%. The results are shown in FIG. 5. It should be noted that the term "without organic solvent" in FIG. 5 means a case where the bacterial cell enzyme was reacted in the absence of organic solvents.

As shown in FIG. 5, it was found that the use of chloroform or a mixture of chloroform and xylene promoted the incorporation of [$^3$H] GalNAc when the bacterial cell enzyme was used.

Besides, in order to examine the concentration dependency in the case of using chloroform as an organic solvent, the same test as Example 3 was performed by setting chloroform concentration in the enzyme reaction solution to 0, 0.5, 1.0, 2.0, 5.0, or 10.0%, thereby the amount of incorporation of [$^3$H] GalNAc in the polymer fraction was examined. The results are shown in FIG. 6.

Figure 6:
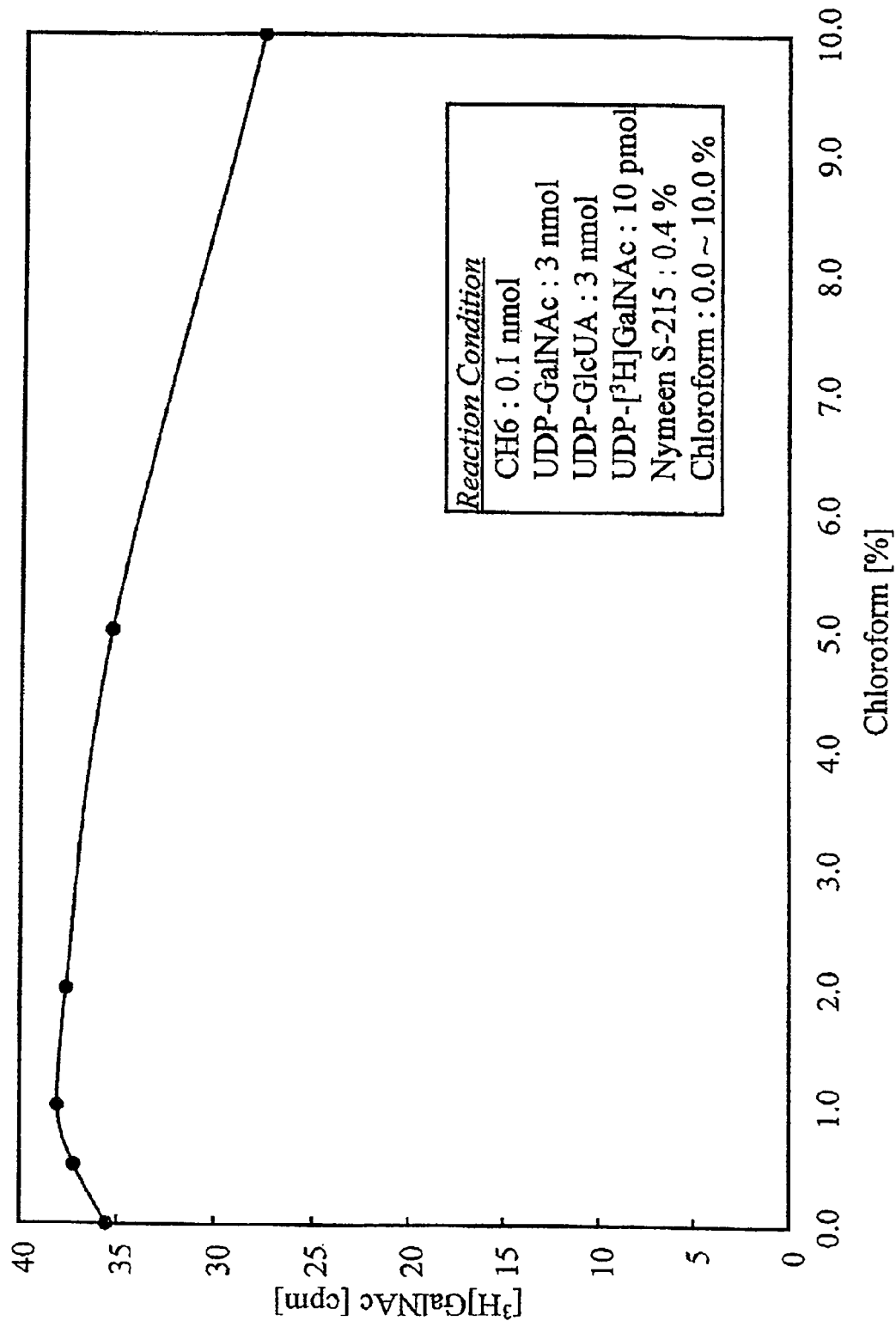
FIG. 6 shows the dependence of CH synthesis on the concentration of organic solvents.

As shown in FIG. 6, it was found that the incorporation of [$^3$H] GalNAc was promoted, when the bacterial cell enzyme was used and chloroform concentration in the enzyme reaction solution was adjusted to more than 0% to less than 5%.

Example 8

Subcloning of kfoA and kfoF and Construction of the Expression Vector

By using a DNA sequence of the gene cluster Region 2 (R-II) of *E. coli* K4 strain described in JP 2003-199583 as a template, cDNAs of the UDP-Glc-4-epimerase gene (kfoA) derived from *E. coli* and the UDP-Glc dehydrogenase gene (kofF) derived from *E. coli* were obtained by PCR method. The obtained DNAs were used as templates to perform PCR as follows using the following primers.

```
kfoA-SP: CGGGATCCCGATGAATATATTAGTTACAGG (the underlined part
is a BamHI site, SEQ ID NO: 5)

kfoA-AS: CCCAAGCTTGGGTAGAAGTTATCGTAAAAT (the underlined part is a
HindIII site, SEQ ID NO: 6)

kfoF-SP: CGGGATCCCGATGAAAATTGCAGTTGCTGG (the underlined part is a BamHI
site, SEQ ID NO: 7)

kfoF-AS: CCCAAGCTTGGGTCTTTAATAGCCATAAAA (the underlined part is a
HindIII site, SEQ ID NO: 8)
```

To 100 ng of the template, TakaRa Ex Taq 2.5 Unit (manufactured by TAKARA BIO INC.), 10 μl of 10×Ex Taq Buffer, 8 μl of 2.5 mM dNTP Mixture, and 100 pmol each of sense primer and antisense primer were added to adjust the total volume to 100 μl with milli-Q water. The PCR condition was as follows. After a reaction was carried out at 94° C. for 5 minutes, a cycle of 94° C. for 30 seconds, 55° C. for 1 minute, and 72° C. for 90 seconds was repeated 30 times, and thereafter another reaction was performed 72° C. for 7 minutes.

The reaction solution was subjected to gel extraction to extract the target fragments with QIA quick (manufactured by QIAGEN GmbH), and the fragments were subject to limited digestion with BamHI and HindIII overnight. After that, the resultant was again subject to gel extraction to purify the target fragments. To about 100 ng of pTric-His C vector (manufactured by Invitrogen Corporation) subjected to limited digestion with the same restriction enzymes, about 300 ng of the purified cDNA fragments, 0.5 μl of T4 ligase (manufactured by New England Biolabs Inc.), and 1 μl of 10×T4 ligase Buffer were added to adjust the total volume to 10 μl with milli-Q water. The resultant was subjected to ligation for 1 hours in water bath of 16° C. Then, 100 μl of competent cells of TOP10 were transformed using 5 μl of the reaction solution. The resultant was applied on ampicillin-containing LB agar medium (LB/Amp plate) and left standing at 37° C. overnight.

After 5 colonies were selected arbitrary out of colonies on the plate, plasmids were extracted by an alkaline prep method to perform an insert check with BamHI and HindIII. The sequence of the plasmid into which the insert was correctly incorporated was confirmed to recognize that the sequence is not different from the gene sequence of the database (GeneBank accession No. AB079602). The confirmed DNA sequences of UDP-Glc-4-epimerase gene (kfoA) derived from *E. coli* K4 strain and the UDP-Glc dehydrogenase gene (kofF) derived from *E. coli* K4 strain are shown in SEQ ID NO: 1 and SEQ ID NO: 3, respectively, together with the amino acids encoded by each of the genes. The amino acid sequences of the UDP-Glc-4-epimerase and the UDP-Glc dehydrogenase encoded by these genes are shown in SEQ ID NO: 2 and SEQ ID NO: 4, respectively.

Example 9

Preparation of the Recombinant Kfoa and Recombinant KfoF And Detection of Activities Thereof Each of the expression vectors of KfoA and KfoF was introduced to transform *E. coli* TOP10, and each of the transformed *E. coli* TOP10 was cultured in 100 ml of ampicillin-containing LB liquid medium at 37° C. until O.D.600 reached 0.5. To the medium, IPTG was added so as to have a final concentration of 1 mM, and expression was induced for 3 hours. Then, soluble fractions obtained by sonication treatment were passed through Ni-NTA Agarose column (manufactured by QIAGEN GmbH) to obtain purified enzymes of KfoA and KfoF. The obtained enzyme fractions were dialyzed overnight in 1 L of 20% Glycerol-containing PBS solution. After that, the solution was replaced with new ones to perform 6 hours of dialysis twice.

The enzyme reaction of KfoA was performed by heating a mixed solution of 2.5 μl of the enzyme, 5 μl of 1 mM UDP-GlcNAc, 5 μl of 1 M Tris-HCl, and 37.5 μl of water in a bath at 30° C. for 1 hour. After that, UDP-GlcNAc and UDP-GalNAc were separated with Hydrosphere C18 column (manufactured by YMC Co., Ltd.). The enzyme activity (amount of produced UDP-GalNAc per unit time) was calculated from the area ratio of UDP-GlcNAc to UDP-GalNAc.

The enzyme reaction of KfoF was performed by heating a mixed solution of 5 μl of the enzyme, 5 μl of 1 mM UDP-Glc, 5 μl of 1 M Tris-HCl or Glycine-NaOH, 10 μl of 5 mM 13-NAD$^+$, and 25 μl of water in a bath at 30° C. for 1 hour. After that, UDP-Glc and UDP-GlcUA were separated with Hydrosphere C18 column. The enzyme activity (amount of produced UDP-GlcUA per unit time) was calculated from the area ratio of UDP-Glc to UDP-GlcU.

Recombinant enzymes of KfoA and KfoF produced by an *E. coli* expression system were purified with Ni-NTA Agarose column, and the collected fractions were separated by SDS-PAGE. The expression of the recombinant enzymes was confirmed by Western Blotting using the mouse Tetra His tag antibody (manufactured by QIAGEN GmbH) as a primary antibody and the Goat Anti Mouse HRP antibody (manufactured by Gibco BRL) as a secondary antibody. As a result, KfoA was detected as a main band with a specific dye at the position of 42 kDa including the molecular weight of His tag. KfoF was detected as a main band with a specific dye at the position of 48 kDa. Further, when the gel after SDS-PAGE was dyed with CBB, densely-dyed bands other than those bands were not found. The collected enzymes were dialyzed with 20% glycerol-containing PBS solution three times, and the enzymes were stored at −80° C.

Optimal reaction conditions were studied using the produced recombinant enzymes of KfoA and KfoF. A reaction solution (50 μl) containing 2.5 μl of KfoA, 5 nmol of UDP-GlcNAc, and Tris-HCl (pH of 7.0 to 10.0) at a final concentration of 1 M was heated for 1 hour in water bath at 30° C. After that, the produced UDP-GalNAc and unreacted UDP-GlcNAc were separated using Hydrosphere C18 reverse-phase column. The rate of UDP-GalNAc with respect to the total nucleotide amount was quantified based on the area ratio of two peaks. As a result, Tris-HCl having pH of 8.5 was determined to be the optimal buffer solution for KfoF because UDP-GalNAc was produced most at pH 8.5.

As for KfoF, a reaction solution (50 μl) containing 5 μl of KfoF, 5 nmol of UDP-Glc, 50 nmol of β-NAD$^+$, and 0.1 M Tris-HCl (pH of 7.0 to 10.0) or 0.1 M glycine-NaOH (pH of 9.0 to 10.0) was heated for 1 hour in water bath at 30° C. Then, absorbance at 340 nm was measured by the absorptiometer to relatively compare the enzyme activity at each pH. The absorbance at 340 nm is derived from two molecules of β-NADH that are generated when a molecule of UDP-Glc is oxidized, so the absorbance is in proportion to the enzymatic activity of KfoF. As a result, because the absorbance reached maximum at the time of reaction with glycine-NaOH having pH of 9.4, glycine-NaOH having pH of 9.4 was determined to be the optimal buffer solution for KfoF.

Example 10

CH Polymer Synthesis by the Three Kinds of Bacterial Cell Enzyme Reactors

Figure 7:
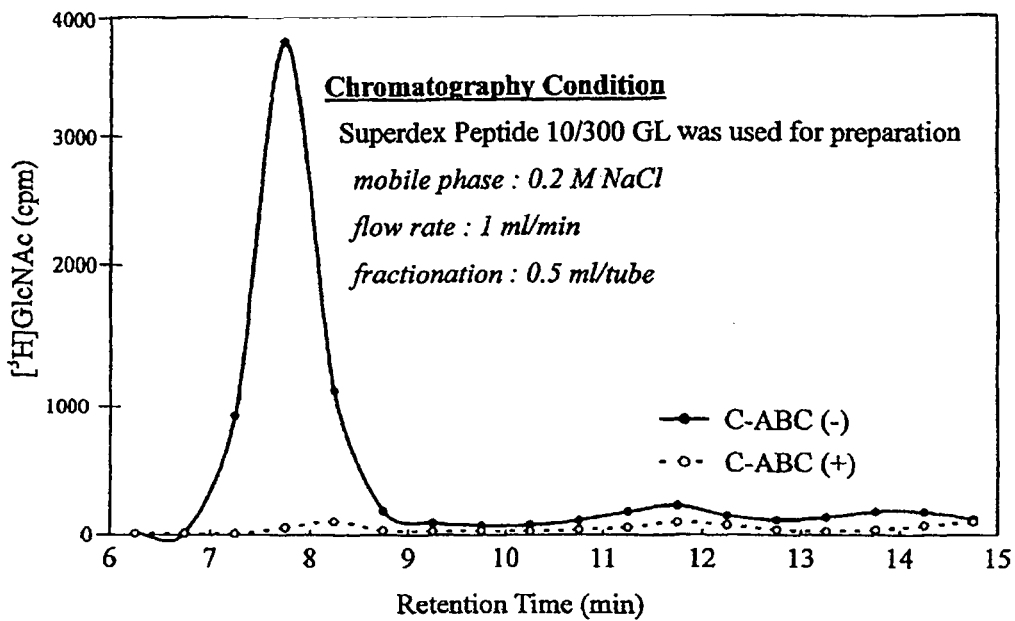
FIG. 7 shows the elution curves of the product obtained in Example 10 and the product treated with chondroitinase ABC when the elution was performed with Superdex Peptide column.

In the same manner as in Example 1, each of the expression vectors of KfoA and KfoF was introduced to transform *E. coli* TOP10, and each of the transformed *E. coli* TOP10 was cultured in 100 ml of ampicillin-containing LB liquid medium at 37° C. until O.D. 600 reached 0.5. To the medium, IPTG was added so as to have a final concentration of 1 mM, and expression was induced for 3 hours. 1 ml each of the media was dispensed, and each medium was centrifuged at 15,000×g for 1 minute to remove the supernatant. Each of the resultants was stored at −80° C. to be used as bacterial cell enzymes for KfoA and KfoF. These two kinds of bacterial reactors were mixed with K4CP bacterial cell enzyme obtained in Example 1. To the mixture, 0.1 nmol of CH6, 3 nmol (0.1 μCi) of UDP-[$^3$H] GlcNAc, 3 nmol of UDP-Glc, and 30 nmol of (3-NAD$^+$ were added, and the total amount of 100 μl of solution containing 150 mM NaCl, 0.2 mM MnCl$_2$, 50 mM Tris-HCl (pH of 8.5), and 0.4% Nymeen S-215 (surfactant) was prepared. The solution was subjected to synthesis reaction at 30° C. overnight while being strongly stirred. The reaction solution was boiled for 10 minutes, followed by centrifugation at 15,000×g for 1 minute. The supernatant was filtered through a filter having 0.45 μm of pore diameter (manufactured by Millipore Corporation). Each sample was subjected to size fractionation with Superdex Peptide 10/300 GL (manufactured by Amersham Biosciences Co., Ltd.). After that, $^3$H content of each fraction was measured with a scintillation counter to confirm the synthesis of CH polymers. An elution curve of the product in Superdex Peptide column is shown in FIG. 7 (C-ABC (−)). In addition, after the product was treated with chondroitinase ABC, ³H content of each fraction was measured with a scintillation counter in the same manner as described above. The elution curve of the product treated with chondroitinase ABC in Superdex Peptide column is shown in FIG. 7 (C-ABC (+)). By the treatment of the product with chondroitinase ABC, polymer peaks have disappeared, so it was found that the obtained polymers were CH polysaccharides (FIG. 7).

Figure 8:
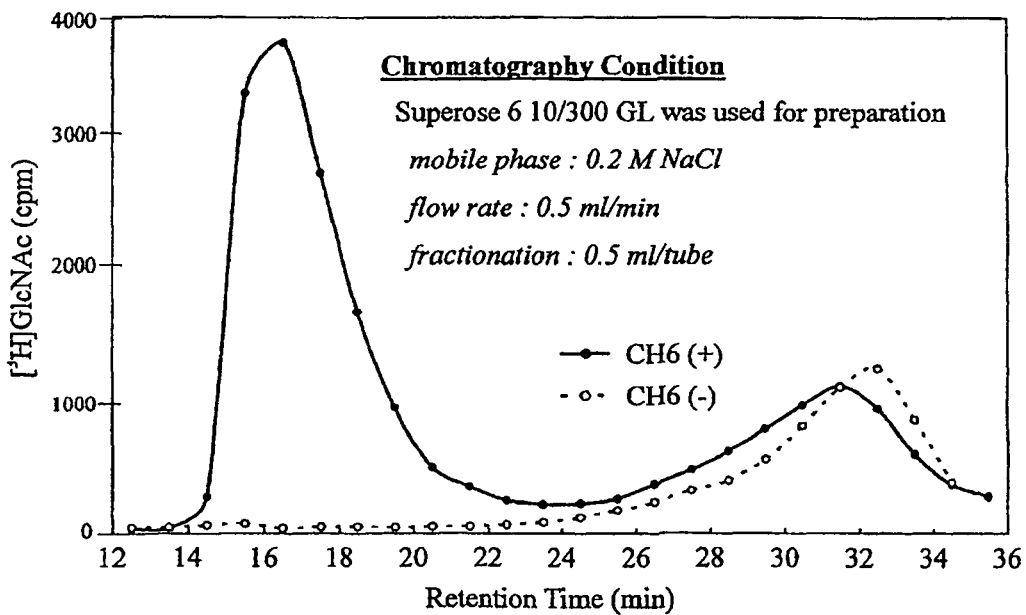
FIG. 8 shows the elution curve of the product obtained by addition of CH6 in CH synthesis in Example 10 and the elution curve of the product obtained without addition of CH6 when the elution was performed with Superose column.

CH was synthesized in the same manner as described above except that CH6 was not added. Elution curves of the products with addition of CH6 and without addition of CH6 in Superose 6 10/300 GL column are shown in FIG. 8 (CH6 (+) and CH6 (−)). When CH6 was not added, a polymer having chondroitinase-degradable property was not obtained even if similar operation was performed, so it was found that CH6 was essential for extension of CH sugar chains (FIG. 8).

From the above-mentioned results, it was confirmed that the synthesis system using these three enzyme reactors synthesized super-high-molecular CH polymers by extension of CH6 as a receptor substrate using UDP-Glc and UDP-GlcNAc as donor substrates.

INDUSTRIAL APPLICABILITY

The method of the present invention can be used for production of a polymer CH sugar chain, and the produced polymer CH is useful as a functional molecule for pharmaceutical, food, cosmetic, and the like.

What is claimed is:

1. A method for producing a chondroitin sugar chain, comprising reacting a glucuronic acid donor, an N-acetyl galactosamine donor, a sugar receptor, and a bacterial cell containing an enzyme which synthesizes chondroitin in a reaction system in the presence of a surfactant selected from the group consisting of polyoxyethylene octadecyl amine, n-decanoyl-N-methylglucamide, sodium cholate, n-octyl-β-D-thioglucopyranoside, n-nonyl-β-D-thiomaltopyranoside, sucrose monocholate, sucrose monocaprate, and sucrose monolaurate.

2. The method according to claim 1, wherein the bacterial cell containing an enzyme which synthesizes chondroitin expresses a chondroitin polymerase derived from *E. coli*.

3. The method according to claim 2, wherein the chondroitin polymerase derived from *E. coli* is K4CP.

4. The method according to claim 2, wherein the bacterial cell containing an enzyme that expresses chondroitin synthase derived from *E. coli* is an *E. coli* cell.

5. The method according to claim 4, wherein the *E. coli* cell is an *E. coli* TOP10 strain cell.

6. The method according to claim 1, wherein the surfactant is selected from the group consisting of polyoxyethylene octadecyl amine, n-nonyl-β-D-thiomaltopyranoside, sucrose monocaprate, and sucrose monolaurate.

7. The method according to claim 1, wherein the surfactant is selected from the group consisting of n-nonyl-β-D-thiomaltopyranoside, sucrose monocaprate, and sucrose monolaurate.

8. The method according to claim 1, wherein the reaction is performed for 1 hour to 10 days at 10 to 50° C.

9. The method according to claim 1, wherein the reaction is performed for 10 to 30 hours at 20 to 40° C.

10. The method according to claim 1, wherein the reaction is performed for 15 to 24 hours at 20 to 40° C.

11. The method according to claim 1, wherein the reaction is performed for 15 to 24 hours at 25 to 37° C.

12. The method according to claim 1, wherein the glucuronic acid donor is UDP-glucuronic acid, and the N-acetyl galactosamine donor is UDP-N-acetyl galactosamine.

13. The method according to claim 12, wherein the reaction system further comprises UDP-glucose-4-epimerase, UDP-N-acetyl glucosamine, UDP-glucose dehydrogenase and UDP-glucose and wherein UDP-N-acetyl galactosamine is the N-acetyl galactosamine donor and UDP-glucuronic acid is the glucuronic acid donor.

14. The method according to claim 1, wherein the reaction system further comprises one or more organic solvents selected from the group consisting of xylene, chloroform, paraffin and formaldehyde.

15. The method according to claim 14, wherein the one or more organic solvents are selected from the group consisting of chloroform, xylene and the combination thereof.

16. The method according to claim 14, wherein the concentration of the one or more organic solvents is more than 0% and less than 5%.

17. The method according to claim 1, wherein the chondroitin sugar chain that is produced by the reaction has all the following characteristics (1) to (3):

(1) wherein the chondroitin sugar chain has a weight average molecular weight is 50,000 Da or more measured by gel filtration chromatography;

(2) wherein the chondroitin sugar chain is completely degradable into disaccharides with chondroitinase ABC; and (3) wherein when the chondroitin sugar chain is decomposed with chondroitinase ABC to form decomposed product products, all of the decomposed products substantially correspond to chondroitin unsaturated disaccharides.

18. The method according to claim 17, wherein the weight average molecular weight is 75,000 Da or more.

19. The method according to claim 18, wherein the weight average molecular weight is 200,000 Da or more.

* * * * *

UNITED STATES PATENT AND TRADEMARK OFFICE
CERTIFICATE OF CORRECTION

PATENT NO.       : 8,067,204 B2
APPLICATION NO.  : 12/097725
DATED            : November 29, 2011
INVENTOR(S)      : Sugiura et al.

It is certified that error appears in the above-identified patent and that said Letters Patent is hereby corrected as shown below:

Page 1, Item (56) References Cited, Column 2, Line 12 (Other Publications), "factores." should be changed to --factories.--

Page 1, Item (56) References Cited, Column 2, Line 17 (Other Publications), "surfactatn" should be changed to --surfactant--

In the drawings: Sheet 3 of 7, (Fig. 3), Line 1, "UDP-G 3 nmole" should be changed to --UDP-G 3 nmol--

In the drawings: Sheet 3 of 7, (Fig. 3), Line 2, "UDP-G 30nmole" should be changed to --UDP-G 30 nmol--

In the drawings: Sheet 4 of 7, (Fig. 4), Line 14, "Dodecyl-maltocside" should be changed to --Dodecyl-maltoside--

Column 1, Line 52, "pain and arthragia," should be changed to --pain and arthralgia,--

Column 3, Line 14, ""UDP-Glc4-epimerase" should be changed to --UDP-Glc4-epimerase--

Column 5, Line 7, "(deoxythymidine5'-diphosphate)-GalNAc" should be changed to --(deoxythymidine-5'-diphosphate)-GalNAc--

Column 5, Line 35, "CH octosaccharide," should be changed to --CH octasaccharide,--

Column 7, Line 9, "pEZZZ18," should be changed to --pEZZ18,--

Column 10, Line 23, "prepared. the plasmid" should be changed to --prepared. The plasmid--

Column 12, Line 43, "Tween20" should be changed to --Tween 20--

Column 12, Line 55, "(3-[3-cholamidepropyl)" should be changed to --(3-[3-cholamidopropyl)--

Column 12, Line 65, "(3-[3-cholamidepropyl)" should be changed to --(3-[3-cholamidopropyl)--

Column 13, Line 8, "(n-octyl-3-D-glucopyranoside," should be changed to --(n-octyl-β-D-glycopyranoside,--

Column 14, Line 22, "(kofF) derived" should be changed to --(kfoF) derived--

Signed and Sealed this
Twelfth Day of June, 2012

David J. Kappos
*Director of the United States Patent and Trademark Office*

CERTIFICATE OF CORRECTION (continued)
U.S. Pat. No. 8,067,204 B2

Column 15, Line 3, "(GeneBank" should be changed to --(GenBank--

Column 15, Line 6, "(kofF) derived" should be changed to --(kfoF) derived--

Column 15, Line 16, "Kfoa and" should be changed to --KfoA and--

Column 29, Line 1, "product products, all of the" should be changed to --products, all of the--

SEQUENCE LISTING

```
<160> NUMBER OF SEQ ID NOS: 8

<210> SEQ ID NO 1
<211> LENGTH: 1020
<212> TYPE: DNA
<213> ORGANISM: Escherichia coli
<220> FEATURE:
<221> NAME/KEY: CDS
<222> LOCATION: (1)..(1020)

<400> SEQUENCE: 1 atg aat ata tta gtt aca ggt gga gca ggc tat att ggc tcg cat act       48
Met Asn Ile Leu Val Thr Gly Gly Ala Gly Tyr Ile Gly Ser His Thr
1               5                   10                  15 agt tta tgt ctt ctg aat aaa ggt tac aat gtt gta atc att gac aac       96
Ser Leu Cys Leu Leu Asn Lys Gly Tyr Asn Val Val Ile Ile Asp Asn
            20                  25                  30 tta att aat tca tct tgc gag agc att cga agg att gaa tta ata gct      144
Leu Ile Asn Ser Ser Cys Glu Ser Ile Arg Arg Ile Glu Leu Ile Ala
        35                  40                  45 aaa aaa aaa gtt act ttc tat gag ttg aac atc aac aat gaa aaa gaa      192
Lys Lys Lys Val Thr Phe Tyr Glu Leu Asn Ile Asn Asn Glu Lys Glu
50                  55                  60 gtt aat caa att cta aaa aaa cac aaa ttt gat tgt ata atg cat ttt      240
Val Asn Gln Ile Leu Lys Lys His Lys Phe Asp Cys Ile Met His Phe
65                  70                  75                  80 gcc ggt gca aag tct gtt gct gaa tct tta ata aaa ccc att ttt tat      288
Ala Gly Ala Lys Ser Val Ala Glu Ser Leu Ile Lys Pro Ile Phe Tyr
                85                  90                  95 tat gat aat aat gtt tca ggg acg ttg caa tta att aat tgc gct ata      336
Tyr Asp Asn Asn Val Ser Gly Thr Leu Gln Leu Ile Asn Cys Ala Ile
            100                 105                 110 aaa aac gat gtg gct aat ttt att ttt agc tct tct gca acg gtt tat      384
Lys Asn Asp Val Ala Asn Phe Ile Phe Ser Ser Ser Ala Thr Val Tyr
        115                 120                 125 ggt gaa agc aaa ata atg cct gta aca gaa gat tgc cat ata gga gga      432
Gly Glu Ser Lys Ile Met Pro Val Thr Glu Asp Cys His Ile Gly Gly
    130                 135                 140 aca tta aat cca tat ggt aca tca aag tat ata tca gaa ttg atg att      480
Thr Leu Asn Pro Tyr Gly Thr Ser Lys Tyr Ile Ser Glu Leu Met Ile
145                 150                 155                 160 aga gat att gca aaa aaa tat agc gat act aat ttt ttg tgt ctg aga      528
Arg Asp Ile Ala Lys Lys Tyr Ser Asp Thr Asn Phe Leu Cys Leu Arg
                165                 170                 175 tat ttt aac cca aca ggt gct cac gag tcg gga atg atc ggt gaa agt      576
```

```
                                                                   -continued Tyr Phe Asn Pro Thr Gly Ala His Glu Ser Gly Met Ile Gly Glu Ser
            180                 185                 190 ccc gct gat ata cca agc aat tta gtt cct tat ata tta caa gtt gct      624
Pro Ala Asp Ile Pro Ser Asn Leu Val Pro Tyr Ile Leu Gln Val Ala
            195                 200                 205 atg ggt aaa cta gaa aaa ctt atg gtg ttt ggg ggg gat tac cct aca      672
Met Gly Lys Leu Glu Lys Leu Met Val Phe Gly Gly Asp Tyr Pro Thr
        210                 215                 220 aag gat gga acc ggt gtt cgt gat tat ata cac gta atg gat tta gcg      720
Lys Asp Gly Thr Gly Val Arg Asp Tyr Ile His Val Met Asp Leu Ala
225                 230                 235                 240 gaa ggg cat gtg gct gct tta tct tac ctt ttc cgt gat aat aac act      768
Glu Gly His Val Ala Ala Leu Ser Tyr Leu Phe Arg Asp Asn Asn Thr
                245                 250                 255 aat tat cat gtt ttt aat tta ggt act ggt aaa gga tat tct gtt tta      816
Asn Tyr His Val Phe Asn Leu Gly Thr Gly Lys Gly Tyr Ser Val Leu
            260                 265                 270 gag ctg gtt tct acc ttt gaa aaa ata tct ggg gtt aga att cca tat      864
Glu Leu Val Ser Thr Phe Glu Lys Ile Ser Gly Val Arg Ile Pro Tyr
        275                 280                 285 gaa att gtt tcg aga aga gat ggg gat att gct gaa agt tgg tca tca      912
Glu Ile Val Ser Arg Arg Asp Gly Asp Ile Ala Glu Ser Trp Ser Ser
    290                 295                 300 cca gaa aaa gca aat aag tat ctc aat tgg aaa gct aaa agg gaa ttg      960
Pro Glu Lys Ala Asn Lys Tyr Leu Asn Trp Lys Ala Lys Arg Glu Leu
305                 310                 315                 320 gaa aca atg ctt gag gat gcc tgg cgc tgg caa atg aaa aac cca aat     1008
Glu Thr Met Leu Glu Asp Ala Trp Arg Trp Gln Met Lys Asn Pro Asn
                325                 330                 335 ggt tat att taa                                                     1020
Gly Tyr Ile <210> SEQ ID NO 2
<211> LENGTH: 339
<212> TYPE: PRT
<213> ORGANISM: Escherichia coli

<400> SEQUENCE: 2

Met Asn Ile Leu Val Thr Gly Gly Ala Gly Tyr Ile Gly Ser His Thr
1               5                   10                  15

Ser Leu Cys Leu Leu Asn Lys Gly Tyr Asn Val Ile Ile Asp Asn
            20                  25                  30

Leu Ile Asn Ser Ser Cys Glu Ser Ile Arg Arg Ile Glu Leu Ile Ala
        35                  40                  45

Lys Lys Lys Val Thr Phe Tyr Glu Leu Asn Ile Asn Asn Glu Lys Glu
    50                  55                  60

Val Asn Gln Ile Leu Lys Lys His Lys Phe Asp Cys Ile Met His Phe
65                  70                  75                  80

Ala Gly Ala Lys Ser Val Ala Glu Ser Leu Ile Lys Pro Ile Phe Tyr
                85                  90                  95

Tyr Asp Asn Asn Val Ser Gly Thr Leu Gln Leu Ile Asn Cys Ala Ile
            100                 105                 110

Lys Asn Asp Val Ala Asn Phe Ile Phe Ser Ser Ala Thr Val Tyr
        115                 120                 125

Gly Glu Ser Lys Ile Met Pro Val Thr Glu Asp Cys His Ile Gly Gly
    130                 135                 140

Thr Leu Asn Pro Tyr Gly Thr Ser Lys Tyr Ile Ser Glu Leu Met Ile
145                 150                 155                 160
```

-continued

```
Arg Asp Ile Ala Lys Lys Tyr Ser Asp Thr Asn Phe Leu Cys Leu Arg
            165                 170                 175
Tyr Phe Asn Pro Thr Gly Ala His Glu Ser Gly Met Ile Gly Glu Ser
        180                 185                 190
Pro Ala Asp Ile Pro Ser Asn Leu Val Pro Tyr Ile Leu Gln Val Ala
    195                 200                 205
Met Gly Lys Leu Glu Lys Leu Met Val Phe Gly Gly Asp Tyr Pro Thr
210                 215                 220
Lys Asp Gly Thr Gly Val Arg Asp Tyr Ile His Val Met Asp Leu Ala
225                 230                 235                 240
Glu Gly His Val Ala Ala Leu Ser Tyr Leu Phe Arg Asp Asn Asn Thr
                245                 250                 255
Asn Tyr His Val Phe Asn Leu Gly Thr Gly Lys Gly Tyr Ser Val Leu
            260                 265                 270
Glu Leu Val Ser Thr Phe Glu Lys Ile Ser Gly Val Arg Ile Pro Tyr
        275                 280                 285
Glu Ile Val Ser Arg Arg Asp Gly Asp Ile Ala Glu Ser Trp Ser Ser
    290                 295                 300
Pro Glu Lys Ala Asn Lys Tyr Leu Asn Trp Lys Ala Lys Arg Glu Leu
305                 310                 315                 320
Glu Thr Met Leu Glu Asp Ala Trp Arg Trp Gln Met Lys Asn Pro Asn
                325                 330                 335
Gly Tyr Ile
```

<210> SEQ ID NO 3
<211> LENGTH: 1170
<212> TYPE: DNA
<213> ORGANISM: Escherichia coli
<220> FEATURE:
<221> NAME/KEY: CDS
<222> LOCATION: (1)..(1170)

<400> SEQUENCE: 3

```
atg aaa att gca gtt gct ggt gta gga tat gtt ggt ata tca att gct    48
Met Lys Ile Ala Val Ala Gly Val Gly Tyr Val Gly Ile Ser Ile Ala
1               5                   10                  15 ata tta ctt tca caa aaa cat gat att atc gct ctc gat ata gat cct    96
Ile Leu Leu Ser Gln Lys His Asp Ile Ile Ala Leu Asp Ile Asp Pro
                20                  25                  30 aag aaa gtt cag ttg att aat aaa aaa ata tca cca ata tgt gat cct   144
Lys Lys Val Gln Leu Ile Asn Lys Lys Ile Ser Pro Ile Cys Asp Pro
            35                  40                  45 gaa ata caa aaa ttt tta tct aat aga aaa tta aac cta tat gct aca   192
Glu Ile Gln Lys Phe Leu Ser Asn Arg Lys Leu Asn Leu Tyr Ala Thr
        50                  55                  60 aca gaa aaa tac gaa gcg tat aga gat gct gat tat gtt ata atc gca   240
Thr Glu Lys Tyr Glu Ala Tyr Arg Asp Ala Asp Tyr Val Ile Ile Ala
65                  70                  75                  80 aca cca acc aat tat gat ccc att aat aat aac ttc gat aca ctc tca   288
Thr Pro Thr Asn Tyr Asp Pro Ile Asn Asn Asn Phe Asp Thr Leu Ser
                85                  90                  95 gta gaa tca gta gca tgt gac gta cta agt ata aat cct aat gca act   336
Val Glu Ser Val Ala Cys Asp Val Leu Ser Ile Asn Pro Asn Ala Thr
            100                 105                 110 atc ata att aaa tct aca gtc ccc gtc gga ttt act gaa cga cta aaa   384
Ile Ile Ile Lys Ser Thr Val Pro Val Gly Phe Thr Glu Arg Leu Lys
        115                 120                 125 cgc gat cta aac acg aat aat att atc ttt tcc cca gaa ttt tta cgt   432
Arg Asp Leu Asn Thr Asn Asn Ile Ile Phe Ser Pro Glu Phe Leu Arg
```

```
                          130                 135                 140
gaa ggt aaa gct ctt tat gac aac cta tat cca tct cgt ata gtt gtg      480
Glu Gly Lys Ala Leu Tyr Asp Asn Leu Tyr Pro Ser Arg Ile Val Val
145                 150                 155                 160 gga gag agt agc gaa cga gca aga aag ttc gca gag ctt ctc agt gaa      528
Gly Glu Ser Ser Glu Arg Ala Arg Lys Phe Ala Glu Leu Leu Ser Glu
                165                 170                 175 ggc gct ata aaa aaa gat att cca ata ttg tta acg gat agc cct gaa      576
Gly Ala Ile Lys Lys Asp Ile Pro Ile Leu Leu Thr Asp Ser Pro Glu
            180                 185                 190 gct gaa gcc att aaa ctt ttt gca aat act tac ctt gca atg cgg att      624
Ala Glu Ala Ile Lys Leu Phe Ala Asn Thr Tyr Leu Ala Met Arg Ile
        195                 200                 205 gct tat ttc aat gaa ttg gat act tat gcc tcc gtt cat ggt tta gat      672
Ala Tyr Phe Asn Glu Leu Asp Thr Tyr Ala Ser Val His Gly Leu Asp
    210                 215                 220 aca aag caa att ata gag ggt gtt agt tta gat cct aga att ggt caa      720
Thr Lys Gln Ile Ile Glu Gly Val Ser Leu Asp Pro Arg Ile Gly Gln
225                 230                 235                 240 cat tat aat aat cct tct ttt ggt tat gga ggt tac tgc tta cct aag      768
His Tyr Asn Asn Pro Ser Phe Gly Tyr Gly Gly Tyr Cys Leu Pro Lys
                245                 250                 255 gat acc aag caa tca ctc gca aat tat cgt gat gtt ccg cag aac tta      816
Asp Thr Lys Gln Ser Leu Ala Asn Tyr Arg Asp Val Pro Gln Asn Leu
            260                 265                 270 atc cag gct att gtc gat gcc aat act acc cga aaa gac ttt gtt gcg      864
Ile Gln Ala Ile Val Asp Ala Asn Thr Thr Arg Lys Asp Phe Val Ala
        275                 280                 285 gag gat ata tta agt cgt aaa cca aaa gtt gta gga atc tat cgc ctc      912
Glu Asp Ile Leu Ser Arg Lys Pro Lys Val Val Gly Ile Tyr Arg Leu
    290                 295                 300 ata atg aaa gca ggt agt gat aac ttt aga gca agt agt att caa ggt      960
Ile Met Lys Ala Gly Ser Asp Asn Phe Arg Ala Ser Ser Ile Gln Gly
305                 310                 315                 320 gta atg aaa cga ctc aaa gcc aaa gga att gag ata gtt gta tat gaa     1008
Val Met Lys Arg Leu Lys Ala Lys Gly Ile Glu Ile Val Val Tyr Glu
                325                 330                 335 cct gta cta aaa gag cct tat ttc ttt ggt tct tat gtt gag cgt gat     1056
Pro Val Leu Lys Glu Pro Tyr Phe Phe Gly Ser Tyr Val Glu Arg Asp
            340                 345                 350 att aat tct ttt aaa gaa cgt gtt gat gtt ata gta gcc aat cgc cgc     1104
Ile Asn Ser Phe Lys Glu Arg Val Asp Val Ile Val Ala Asn Arg Arg
        355                 360                 365 acg tca gaa tta gaa gat gta agt gaa aaa gtt tat acg cga gat tta     1152
Thr Ser Glu Leu Glu Asp Val Ser Glu Lys Val Tyr Thr Arg Asp Leu
    370                 375                 380 ttt ggt gtc gac tct tga                                             1170
Phe Gly Val Asp Ser
385

<210> SEQ ID NO 4
<211> LENGTH: 389
<212> TYPE: PRT
<213> ORGANISM: Escherichia coli

<400> SEQUENCE: 4

Met Lys Ile Ala Val Ala Gly Val Gly Tyr Val Gly Ile Ser Ile Ala
1               5                   10                  15

Ile Leu Leu Ser Gln Lys His Asp Ile Ile Ala Leu Asp Ile Asp Pro
            20                  25                  30
```

```
Lys Lys Val Gln Leu Ile Asn Lys Lys Ile Ser Pro Ile Cys Asp Pro
         35                  40                  45

Glu Ile Gln Lys Phe Leu Ser Asn Arg Lys Leu Asn Leu Tyr Ala Thr
 50                  55                  60

Thr Glu Lys Tyr Glu Ala Tyr Arg Asp Ala Asp Tyr Val Ile Ile Ala
 65                  70                  75                  80

Thr Pro Thr Asn Tyr Asp Pro Ile Asn Asn Phe Asp Thr Leu Ser
                 85                  90                  95

Val Glu Ser Val Ala Cys Asp Val Leu Ser Ile Asn Pro Asn Ala Thr
                100                 105                 110

Ile Ile Ile Lys Ser Thr Val Pro Val Gly Phe Thr Glu Arg Leu Lys
            115                 120                 125

Arg Asp Leu Asn Thr Asn Asn Ile Ile Phe Ser Pro Glu Phe Leu Arg
130                 135                 140

Glu Gly Lys Ala Leu Tyr Asp Asn Leu Tyr Pro Ser Arg Ile Val Val
145                 150                 155                 160

Gly Glu Ser Ser Glu Arg Ala Arg Lys Phe Ala Glu Leu Leu Ser Glu
                165                 170                 175

Gly Ala Ile Lys Lys Asp Ile Pro Ile Leu Leu Thr Asp Ser Pro Glu
                180                 185                 190

Ala Glu Ala Ile Lys Leu Phe Ala Asn Thr Tyr Leu Ala Met Arg Ile
195                 200                 205

Ala Tyr Phe Asn Glu Leu Asp Thr Tyr Ala Ser Val His Gly Leu Asp
210                 215                 220

Thr Lys Gln Ile Ile Glu Gly Val Ser Leu Asp Pro Arg Ile Gly Gln
225                 230                 235                 240

His Tyr Asn Asn Pro Ser Phe Gly Tyr Gly Gly Tyr Cys Leu Pro Lys
                245                 250                 255

Asp Thr Lys Gln Ser Leu Ala Asn Tyr Arg Asp Val Pro Gln Asn Leu
                260                 265                 270

Ile Gln Ala Ile Val Asp Ala Asn Thr Thr Arg Lys Asp Phe Val Ala
            275                 280                 285

Glu Asp Ile Leu Ser Arg Lys Pro Lys Val Val Gly Ile Tyr Arg Leu
290                 295                 300

Ile Met Lys Ala Gly Ser Asp Asn Phe Arg Ala Ser Ser Ile Gln Gly
305                 310                 315                 320

Val Met Lys Arg Leu Lys Ala Lys Gly Ile Glu Ile Val Tyr Glu
                325                 330                 335

Pro Val Leu Lys Glu Pro Tyr Phe Phe Gly Ser Tyr Val Glu Arg Asp
                340                 345                 350

Ile Asn Ser Phe Lys Glu Arg Val Asp Val Ile Val Ala Asn Arg Arg
                355                 360                 365

Thr Ser Glu Leu Glu Asp Val Ser Glu Lys Val Tyr Thr Arg Asp Leu
370                 375                 380

Phe Gly Val Asp Ser
385
```

<210> SEQ ID NO 5
<211> LENGTH: 30
<212> TYPE: DNA
<213> ORGANISM: Artificial sequence
<220> FEATURE:
<223> OTHER INFORMATION: Primer

<400> SEQUENCE: 5
cgggatcccg atgaatatat tagttacagg                                    30

```
<210> SEQ ID NO 6
<211> LENGTH: 30
<212> TYPE: DNA
<213> ORGANISM: Artificial sequence
<220> FEATURE:
<223> OTHER INFORMATION: Primer

<400> SEQUENCE: 6
cccaagcttg ggtagaagtt atcgtaaaat                                        30

<210> SEQ ID NO 7
<211> LENGTH: 30
<212> TYPE: DNA
<213> ORGANISM: Artificial sequence
<220> FEATURE:
<223> OTHER INFORMATION: Primer

<400> SEQUENCE: 7
cgggatcccg atgaaaattg cagttgctgg                                        30

<210> SEQ ID NO 8
<211> LENGTH: 30
<212> TYPE: DNA
<213> ORGANISM: Artificial sequence
<220> FEATURE:
<223> OTHER INFORMATION: Primer

<400> SEQUENCE: 8
cccaagcttg ggtctttaat agccataaaa                                        30
```